(12) United States Patent
Masotti et al.

(10) Patent No.: US 10,786,682 B2
(45) Date of Patent: Sep. 29, 2020

(54) DEVICE FOR TREATING THE VAGINAL CANAL OR OTHER NATURAL OR SURGICALLY OBTAINED ORIFICES, AND RELATED APPARATUS

(71) Applicant: EL.EN. S.P.A., Calenzano (FI) (IT)

(72) Inventors: Leonardo Masotti, Sesto Fiorentino (IT); Mauro Galli, Sesto Fiorentino (IT); Stefano Modi, Brogo San Lorenzo (IT); Maurizio Scortecci, Prato (IT)

(73) Assignee: EL.EN. S.P.A., Calenzano (FI) (IT)

( * ) Notice: Subject to any disclaimer, the term of this patent is extended or adjusted under 35 U.S.C. 154(b) by 1246 days.

(21) Appl. No.: 14/909,250

(22) PCT Filed: Jul. 28, 2014

(86) PCT No.: PCT/EP2014/066211
§ 371 (c)(1),
(2) Date: Feb. 1, 2016

(87) PCT Pub. No.: WO2015/014811
PCT Pub. Date: Feb. 5, 2015

(65) Prior Publication Data
US 2016/0158573 A1  Jun. 9, 2016

(30) Foreign Application Priority Data

Aug. 1, 2013 (IT) ................................ FI2013A0182
Oct. 22, 2013 (IT) ................................ FI2013A0252

(51) Int. Cl.
*A61N 5/06* (2006.01)
*A61B 18/14* (2006.01)
*A61B 1/303* (2006.01)
*A61B 90/00* (2016.01)
*A61B 17/34* (2006.01)
(Continued)

(52) U.S. Cl.
CPC ............ *A61N 5/0603* (2013.01); *A61B 1/303* (2013.01); *A61B 17/3421* (2013.01); *A61B 17/3494* (2013.01); *A61B 18/1485* (2013.01); *A61B 90/361* (2016.02); *A61N 1/40* (2013.01); *A61B 2017/345* (2013.01); *A61B 2018/00559* (2013.01); *A61B 2018/00994* (2013.01); *A61B 2090/036* (2016.02); *A61B 2090/3618* (2016.02); *A61N 2005/067* (2013.01); *A61N 2005/0611* (2013.01); *A61N 2005/0659* (2013.01); *A61N 2005/0666* (2013.01)

(58) Field of Classification Search
None
See application file for complete search history.

(56) References Cited

U.S. PATENT DOCUMENTS

2014/0135609 A1* 5/2014 Kostenich ............... A61B 1/041
600/407

FOREIGN PATENT DOCUMENTS

| CN | 103211651 A | 7/2013 | |
| EP | 2476460 A1 * | 7/2012 | ........... A61N 5/0603 |

(Continued)

*Primary Examiner* — Carolyn A Pehlke
*Assistant Examiner* — Marjan Saboktakin
(74) *Attorney, Agent, or Firm* — McGlew and Tuttle, P.C.

(57) ABSTRACT

The device for treating the vaginal canal by means of a laser beam comprises a retractor for the wall of the vaginal canal, associated with a scanning system for scanning the laser beam towards the wall by means of a pyramidal mirror for laser beam reflection.

43 Claims, 7 Drawing Sheets

(51) Int. Cl.
*A61N 1/40* (2006.01)
*A61B 18/00* (2006.01)
*A61N 5/067* (2006.01)

(56) References Cited

FOREIGN PATENT DOCUMENTS

| | | | |
|---|---|---|---|
| EP | 2476460 A1 | 7/2012 | |
| EP | 2476460 BI | 10/2013 | |
| GB | 2 129 690 A | 5/1984 | |
| WO | 00/40294 A1 | 7/2000 | |
| WO | 03/01653 A1 | 2/2003 | |
| WO | 2006/093655 A2 | 9/2006 | |
| WO | 2008/111970 A1 | 9/2008 | |
| WO | WO-2008111970 A1 * | 9/2008 | ........... A61B 1/0008 |
| WO | 2010/039464 A1 | 4/2010 | |
| WO | 2011096003 A1 | 8/2011 | |
| WO | 2011096006 A1 | 8/2011 | |
| WO | WO-2011096006 A1 * | 8/2011 | ............ A61B 17/42 |
| WO | 2012/037954 A1 | 3/2012 | |

* cited by examiner

DEVICE FOR TREATING THE VAGINAL CANAL OR OTHER NATURAL OR SURGICALLY OBTAINED ORIFICES, AND RELATED APPARATUS

TECHNICAL FIELD

The present invention relates to the field of electro-medical machines and more in particular to the field of machines and apparatuses using a laser source for treating human body.

STATE OF THE ART

Various applications of laser radiation are well known for surgical, aesthetic or therapeutic treatment of human body. In some applications, laser is used instead of surgical knife as cutting tool. In other applications, laser is used to necrotize tumor tissues, to bio-stimulate the growth of particular tissues, for instance cartilaginous tissue for pain treatment and collagen tissue for aesthetic purposes, for instance for wrinkle reduction, rejuvenation, scalp treatment for hair growth purposes, etc.

WO-A-2011096006 discloses a device for treating vaginal canal by a laser beam. The device comprises a vaginal canal wall retractor, associated to a system for directing the laser beam towards the wall. This allows using the laser beam for treating the mucosa of the vaginal canal. The main purpose of the treatment disclosed in WO-A-2011096006 is to prevent and treat atrophic vaginitis, a condition typical but not exclusive of the post-menopause period that currently is normally treated with oestrogens for short periods. Atrophic vaginitis is a pathological condition characterized by an inflammation of the vaginal mucosa with progressive decrease of the mucosa thickness due to the loss of collagen structure. Atrophic vaginitis is a highly disabling condition responsible for considerable psychological discomfort for women suffering from this condition, due to the associated pain, burn, bleeding, ectropion and due to the impossibility of having normal sexual intercourse (dyspareunia).

The device disclosed in WO-A-2011096006 represents an improvement over the state of the art, but can still be further improved to ameliorate the efficiency thereof and make its use simpler and more comfortable for the patient.

EP-A-2476460 discloses a laser system for non-ablative treatment of mucosa tissue. In one embodiment, the system comprises a refractor containing a planar mirror. The planar mirror reflects an impinging laser beam sideways towards the wall of a cavity being treated. The laser beam is controlled to be moved according to a treatment pattern. In another embodiment disclosed in EP-A-2476460, the device comprises a conical mirror. The laser beam is directed coaxially against the conical surface of the conical mirror, which defocusses the laser beam and reflects it over 360° all around the axis of the conical mirror, thus providing a circumferential irradiation of a cylindrical irradiation area on a target area surrounding the retractor wherein the conical mirror is arranged. The shape of the conical mirror defocusses the laser beam thus reducing the effectiveness thereof on the surrounding tissue.

SUMMARY OF THE INVENTION

According to a first aspect, the invention substantially provides a device for laser treatment of the vaginal canal in particular and in general of both natural and surgically obtained orifices, of the animal or human body. The device comprises a retractor for the wall of the vaginal canal or other orifice associated with a system for scanning a laser beam towards the wall of the cavity, canal or orifice. The device advantageously comprises a laser beam reflection mirror, which is preferably pyramidal or truncated pyramidal and preferably fixed with respect to the retractor. The laser beam reflection mirror can be located near a distal end of the retractor. More in general, the laser beam reflection mirror is provided with a plurality of flat, i.e. planar reflecting surfaces, formed by the planar side surfaces of the pyramidal laser beam reflection mirror. The planar reflecting surfaces are inclined with respect to the refractor axis to deviate the laser beam directed by a laser scanning system towards the planar reflecting surfaces of the laser beam reflection mirror. The inclined planar reflecting surfaces deviate the laser beam towards the outside, i.e. against the tissue of the cavity or canal under treatment wherein the retractor has been inserted. The laser beam is deviated in a direction preferably approximately orthogonal to the retractor axis. As it will be clearly apparent from the description below of some embodiments, the pyramidal, truncated-pyramidal allows to treat a surface extending for a given angle, also for 360° around the retractor axis, by moving the laser beam controlled by the laser scanning system, without the need for the refractor to be rotated. In this way the treatment is easier to be performed and more comfortable for the patient.

From an optical viewpoint the use of a pyramidal laser beam reflection mirror instead of a conical mirror is particularly advantageous. The planar reflecting surfaces reflect a focused laser beam directed against the surfaces by the laser scanning system. The reflected laser beam remains focused and is thus particularly efficient in treating the tissue of the canal or cavity being treated with the device. The shape of the laser spot (i.e. the cross sectional form and energy distribution) remains substantially equal after reflection by the planar reflecting surface of the pyramidal or truncated pyramidal laser reflection mirror. It is thus possible to control the laser beam by means of the laser scanning system, such that the laser beam is moved according to a pre-determined pattern on the reflecting surfaces and thus on the targeted tissue surface. A fractional treatment of the tissue forming the wall of the canal or cavity under treatment becomes possible, with an accurate control of the laser irradiation parameters in each irradiated spot.

The use of a plurality of planar reflecting surfaces arranged according to a pyramidal or truncated pyramidal arrangement is particularly advantageous since the laser beam can be moved sequentially on each one of the reflecting surfaces, thus treating the entire surrounding tissue around 360° without rotating the retractor around its axis. The treatment becomes easier for the operator, quicker and causes less discomfort for the patient.

The laser beam is controlled so as to move according to a pattern on each reflecting planar surface of the laser reflection mirror and moves from one reflecting surface to the other very quickly, so that treatment of each circumferentially extending tissue portion becomes fast and does not require but one rotation, if any, of the retractor inside the canal or cavity under treatment.

As will become apparent from the following description of exemplary embodiments of the invention, the laser spot can be moved according to a pattern on each planar reflecting surface until the pattern is completed and then moves on the next reflecting surface, repeating thereon the required pattern. In other embodiments, the laser beam can be moved sequentially onto the various reflecting surfaces more than once, each time performing a part of the pattern on each reflecting surface.

The retractor advantageously has an open window extending for about 360° around the retractor axis, substantially in correspondence of the reflecting surface or surfaces of the pyramidal laser beam reflection mirror. Open window means a window devoid of closing materials, so that the laser beam, deviated by the reflecting surfaces of the pyramidal or truncated pyramidal laser beam reflection mirror, impinges against the wall of the cavity, canal or orifice, this wall being usually formed by tissues that in this way directly face the laser beam reflection mirror, without foreign material interposed between the reflecting surface or surfaces and the tissue. In this way, the laser beam does not need to pass through a window made of any material. It is therefore not necessary to select materials for closing the window that are transparent to the useful wavelength of the laser beam. In fact, it could be possible that these materials are not compatible with the medical use because they are toxic or not suitable for the contact with the patient's tissues.

In an improved embodiment, the retractor comprises an image acquiring device for acquiring images of the treated canal or orifice. This image acquisition system may comprise an image acquisition mirror. In some embodiments the image acquisition mirror is conical, i.e. it has a conical reflecting surface, and is preferably coaxial with the pyramidal or truncated-pyramidal laser beam reflection mirror reflecting the laser beam. Inside the laser beam reflection mirror a camera or a micro-camera may be arranged, acquiring images reflected by the image acquisition mirror. Furthermore, also a lighting system may be housed inside the pyramidal or truncated-pyramidal laser beam reflection mirror reflecting the laser beam. In other embodiments lighting can be obtained by means of a light source arranged at a distance from the laser beam reflection mirrors and generating a lighting beam reflected towards the pyramidal or truncated-pyramidal laser beam reflection mirror by means of the laser beam scanning mirrors.

According to a further improved embodiment of the invention, the retractor may be provided with electrodes for radio-frequency treatment of the tissues. The electrodes may have a linear extension, be preferably parallel to one another and preferably parallel to the retractor axis.

Further advantageous features and embodiments are described below and in the attached claims, forming an integral part of the present description.

According to a further aspect, the invention relates to a laser apparatus comprising a laser source, a waveguide and a device as described above. The laser beam generated by the laser source is conveyed by means of the waveguide towards the device. The scanning system, e.g. a pair of scanning mirrors, arranged in the device control the movement of the laser beam along the planar reflecting surfaces of the pyramidal or truncated pyramidal laser reflection mirror.

In this context, waveguide means any system suitable for conveying the laser beam from the source to the applying device. The waveguide may be constituted by an optical fiber system. In other embodiments, the waveguide may comprise hollow tubular elements, inside which the laser beam is directed, by means of suitable deviating mirrors arranged for instance in joints between consecutive tubular elements and movable with respect to one another.

In some advantageous embodiments the laser source is a pulsed source, wherein the pulses have for instance a duration between about 0.1 and about 10 milliseconds, preferably between about 0.2 and about 2 milliseconds, or a continuous source having emission times comprised between 0.5 and 50 milliseconds. The laser radiation may have a wavelength comprised for instance between about 1,000 nm and about 12,000 nm, preferably between about 9,400 and about 10,600 nm and typically equal to 10,600 nm.

The power of the beam emitted by the source is chosen so that the beam has on the mucosa the effect of renewing the epithelium and stimulating the collagen production, as mentioned above. Typically, the power can be comprised between about 2 and about 100 W, preferably between about 10 and about 50 W and more preferably between about 30 and about 50 W.

The apparatus may comprise systems for controlling the scanning mirrors so as to move the pulsed or continuous beam to perform a treatment according to a method providing for investing the mucosa with laser pulses in areas or points adjacent to each other and consecutive along a preset path, wherein the space between scanning points may be preferably comprised between 0 and about 5,000 micrometers, and preferably between about 50 and about 5,000 micrometers and more preferably between about 200 and about 2,000 micrometers. The pulses for each point may be single or multiple. From one to four pulses for each point may be provided.

Further advantageous features and embodiments of the invention are set forth in the appended claims, which form an integral part of the present description, and will be clearly apparent from the description below of an embodiment of the apparatus and the device according to the invention.

BRIEF DESCRIPTION OF THE DRAWINGS

The invention shall now be more apparent by following the description and accompanying drawing which shows a practical embodiment of the invention. More in particular.

DETAILED DESCRIPTION OF AN EMBODIMENT OF THE INVENTION

Figure 1:
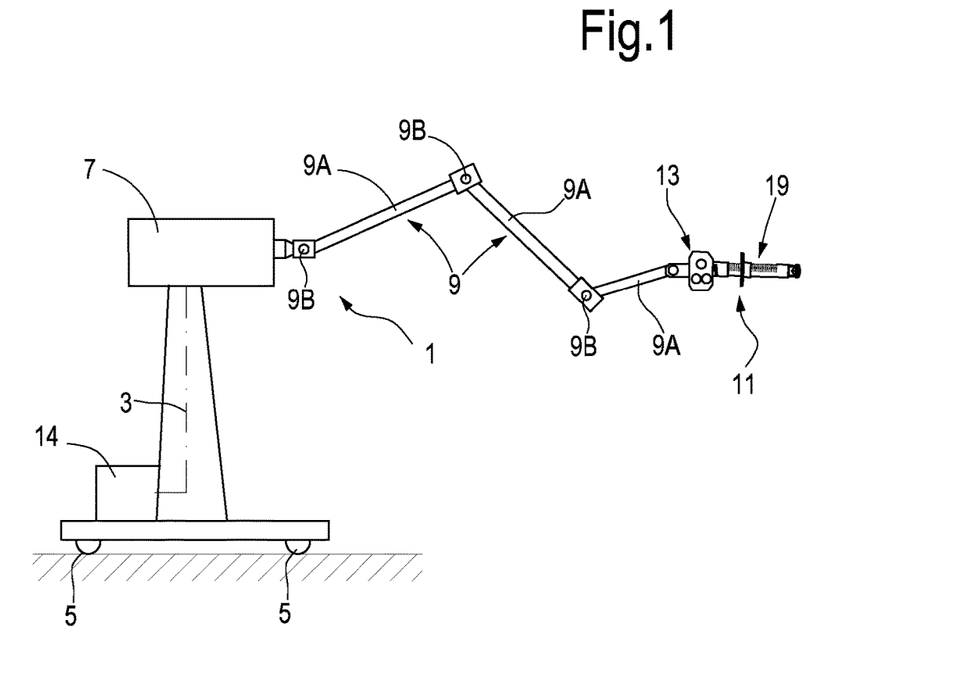
FIG. 1 is a schematic of the apparatus in one embodiment.

FIG. 1 shows a schematic of an apparatus according to the invention. The apparatus, indicated as a whole with number 1, has a support 3 provided for instance with wheels 5 so as to be moved on the floor. A laser source 7 is located on the support 3; the laser source is connected, by means of a waveguide 9, with a treatment device 11. In some embodiments the waveguide 9 is formed by tubular segments 9A joined together by means of known articulated elements 9B to allow the device 11 to be positioned and moved. In the articulated elements scanning mirrors may be provided for directing the laser beam along consecutive tubular segments. The device 11 is at the terminal end of the waveguide.

Figure 2:
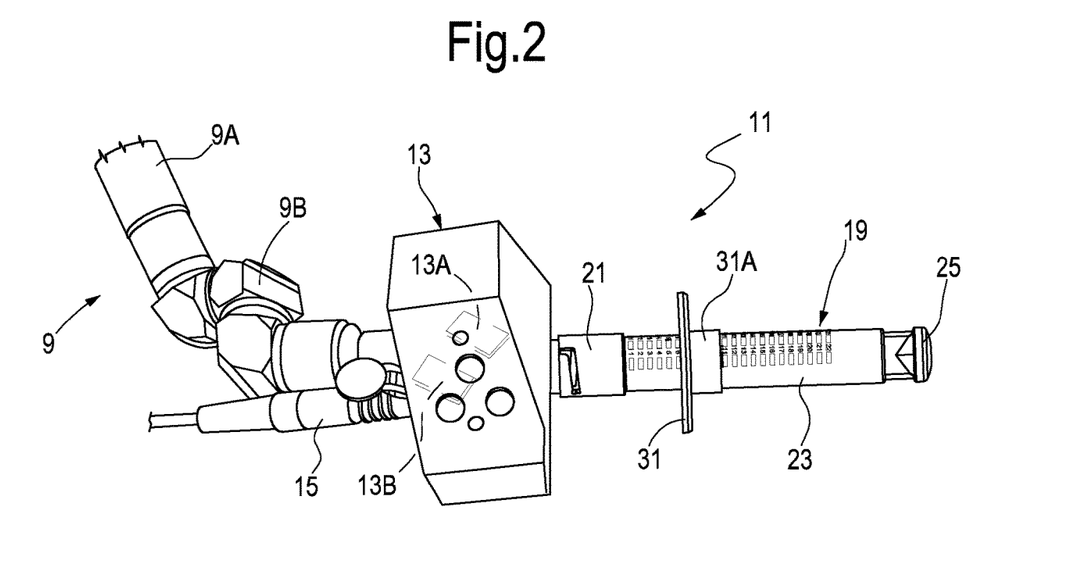
FIG. 2 is a schematic view of the end part of the articulated arm of the apparatus of FIG. 1, the scanning system and the retractor.
Figure 3:
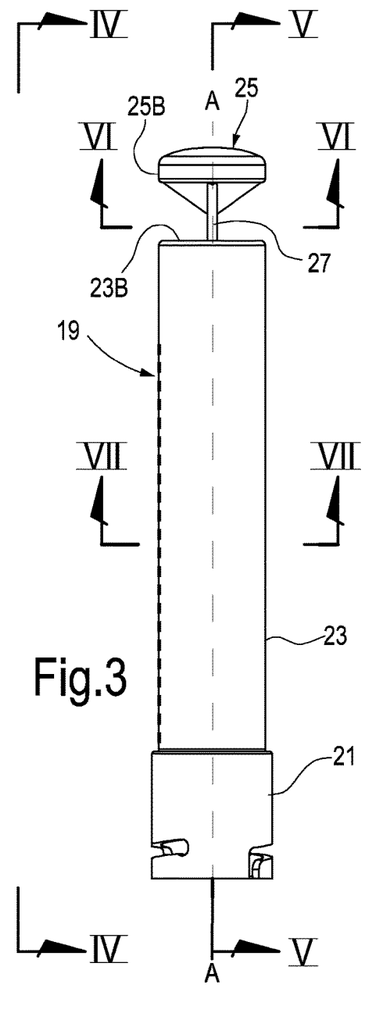
FIG. 3 is a side view of the retractor, separated from the remaining part of the apparatus.
Figure 4:
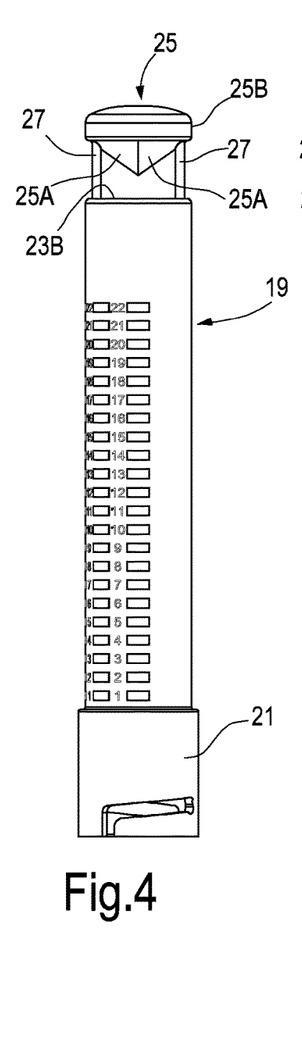
FIG. 4 is a view according to IV-IV of FIG. 3.

The device 11 is shown in detail in FIG. 2. It comprises a box-shaped body forming a housing 13, inside which a laser scanning system is arranged. According to some embodiments, the laser scanning system can comprise scanning mirrors. Two scanning mirrors 13A and 13B are schematically shown with broken lines in the illustrated example. The movement of the scanning mirrors around their axes of rotation is controlled by respective actuators, for instance galvanometers, under the control of a central unit 14, arranged for instance on the support 3 and connected to the device 11 via a cable 15. The control unit 14 is also connected to the laser source 7 to control the emission thereof. Buttons, capacitive sensors or other interface elements may be provide on the box-shaped body forming the housing 13, allowing the user to handle the apparatus and to control the laser emission.

A retractor indicated as a whole with reference number 19 is associated with the housing 13 of the device 11. This retractor can be advantageously reversibly applied to the housing 13, so that it is possible to use retractors 19 differing in shape and dimension and/or to allow sterilization, or else the use of disposable retractors 19 for hygiene and asepsis reasons.

The retractor 19 of the treatment device 11 is shown in detail in FIGS. 3-8.

In some embodiments the retractor 19 has at its distal end anchoring members for fixing it to the housing 13, wherein the scanning mirrors 13A and 13B are located. In the illustrated embodiment the retractor 19 has a bayonet coupling schematically indicated with 21. In other embodiments a different coupling may be provided, for instance a screw coupling. The bayonet coupling has however specific advantages in terms of quickness in coupling and releasing, as well as of easiness in cleaning the retractor 19 after use, as the bayonet coupling 21 does not have areas forming receptacles for microorganisms.

Figure 5:
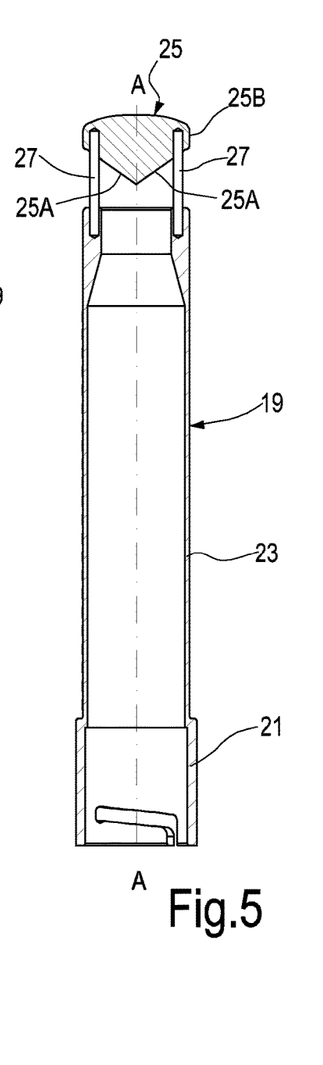
FIG. 5 shows a section according to V-V in FIG. 3.
Figure 6:
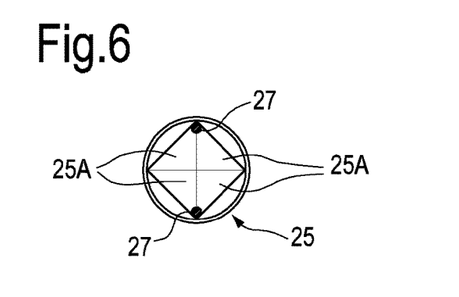
FIGS. 6 and 7 are cross-sections according to VI-VI and VII-VII of FIG. 3.
Figure 7:
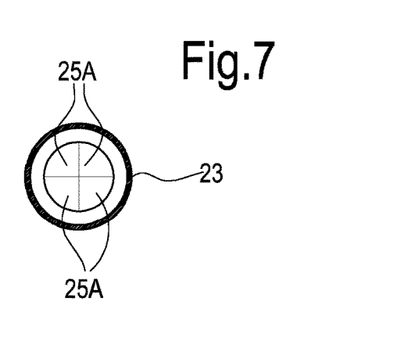

The retractor 19 may have a substantially cylindrical hollow body 23, as shown in particular in the section of FIG. 5. At the opposite end with respect to the bayonet coupling 21 the hollow body 23 of the retractor 19 carries a laser beam reflection mirror, indicated as a whole with reference number 25. The laser beam reflection mirror 25 can be pyramidal or truncated pyramidal and be provided with a plurality of reflecting surfaces 25A. The reflecting surfaces 25A are preferably planar. In some exemplary embodiments four reflecting surfaces 25A can be provided on the laser beam reflection mirror 25. In other embodiments three, five, six, seven, eight or more reflecting surfaces 25A can be provided.

The laser beam reflection mirror 25 may be fixed to the tubular body 23 of the retractor 19, for instance by means of bars 27. In the illustrated embodiment the laser beam reflection mirror 25 and the tubular hollow body 23 are connected together by means of two diametrically opposite bars 27. The bars 27 form spacers supporting the laser beam reflection mirror 25 at a sufficient distance from the end edge of the retractor 19, to form a nearly annular window or slit, where through the laser beam passes. The annular slit or opening formed between the end edge, indicated with 23B, of the tubular hollow body 23 and the base, indicated with 25B, of the pyramidal laser beam reflection mirror 25, is preferably completely open, so that the laser beam, deviated by means of the reflecting surfaces 25A of the pyramidal laser beam reflection mirror 25, propagates in air up to the surface of the surrounding tissue of the vaginal canal in which the refractor 19 is inserted. This allows the application of laser sources with a wavelength that could not pass through closing walls.

For treating the dysfunctions of the vaginal tissue mentioned in the introductory part of the specification, the $CO_2$ laser has been proved to be particularly useful; to its wavelength only toxic materials, such as zinc selenide, are transparent, that are therefore incompatible with this use. It is therefore particularly advantageous to have a free path, i.e. a path in air, for the radiation reflected by the reflecting surfaces 25A of the laser beam reflection mirror 25 to treat the wall of the vaginal canal by means of $CO_2$ laser.

In other embodiments it is also possible to provide a window closed by means of a material transparent to the wavelength of the laser used, in case there are available non toxic materials transparent to the wavelength used. For instance, in the case of treatment with light in or near the visible spectrum, transparent plastics may be used to form walls, where through the path of the reflected laser beam extends. In this case, instead of spacing bars 27, an annular element may be used, made of a material transparent to the laser radiation, interposed between the distal edge 23B of the cylindrical body 23 of the retractor 19 and the base 25B of the laser beam reflection mirror 25.

In advantageous embodiments the mirror 25 is shaped like a pyramid with a regular polygonal base, for instance and preferably with a square base. In other embodiments, not shown, the laser beam reflection mirror 25 may be shaped like a truncated pyramid, also in this case with preferably a regular polygonal base, preferably a square base. It is also possible to use mirrors shaped like a pyramid or a truncated pyramid with different bases, for instance a triangular, a pentagonal or a hexagonal base. The square shape of the base of the pyramid forming the mirror 25 is particularly advantageous and is currently preferred.

In the illustrated embodiment, the pyramidal laser beam reflection mirror 25 with square base has four reflecting surfaces indicated with 25A and formed on the side faces of the pyramid. The two bars 27 are advantageously arranged in correspondence of two corners of the square base of the laser beam reflection mirror 25 and are therefore arranged substantially on a plane where two of the four corners of the pyramid forming the laser beam reflection mirror 25 are located.

With the above described arrangement of the reflecting surfaces 25A the movement of the scanning mirrors 13A, 13B allows to perform a particularly comfortable treatment of the tissue of the vaginal canal inside which the device 11 is inserted. In fact, it is sufficient to move the device 11 only in the longitudinal direction, i.e. parallel to its own axis, for instance moving this device 11 gradually towards the outside after having inserted it completely inside the vaginal canal. Thanks to the movement of the scanning mirrors 13A, 13B controlled by respective galvanometers (known and not shown) the laser beam generated by the laser source is directed from the reflecting surfaces 25A of the laser beam reflection mirror 25 on all the circumferential extension of a given section of the vaginal canal, in correspondence of which the laser beam reflection mirror 25 is positioned each time by means of the longitudinal movement according to incremental steps, for instance guided by means of visible marks provided on the retractor portion visible to the operator. On the contrary of what occurs with other known systems, for instance the system described in WO20110960006, it is not necessary to rotate the device 11 inside the vaginal canal, thus making the use of the apparatus easier for the operator and less invasive for the patient. As it will be specified below, in some cases the retractor 19 shall be rotated only once to have a more uniform treatment.

Figure 10A:
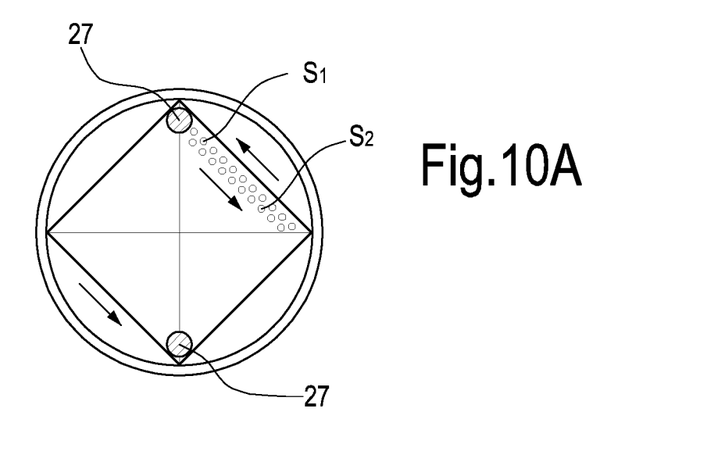
FIG. 10A-10C show the path of the laser radiation spot on the reflecting surfaces of the pyramidal laser beam reflection mirror in possible uses of the device.

The tissue of the vaginal canal may be irradiated for instance by displacing the laser beam by means of the controlled movement of the scanning mirrors 13A, 13B on each of the four planar reflecting surfaces 25A of the mirror 25 sequentially. On each reflecting surface 25A the laser beam can be moved in a direction parallel to the corresponding base edge of the pyramid forming the laser beam reflection mirror 25 and gradually from the base towards the vertex or vice versa, so that the laser beam reflected by the reflecting surface 25A involves a non-infinitesimal portion of tissue. The laser beam can be then sequentially moved on the remaining three faces of the pyramid to work on each of them. This functioning method is schematically represented in FIG. 10A, showing, similar to FIG. 6, a front view of the pyramidal laser beam reflection mirror. The laser beam is controlled by means of the scanning mirrors so as to form a spot moving parallel to the base edge of one of the four faces of the pyramid. In a first phase the laser beam is moved parallel to the base edge and adjacent to it so as to produce a series of spots S1. The laser beam may be actuated in an intermittent pulsed way each time the scanning mirrors 13A, 13B have been positioned to direct the beam in correspondence of one of the spots S1. In correspondence of each spot S1 the beam is deviated, approximately orthogonally to the axis of the retractor 19, towards the side surface of the vaginal canal and nearly orthogonally thereto. Once the row of spots S1 has been completed, the laser beam is moved by means of the scanning mirrors 13A, 13B to form a second row of spots S2, at a greater distance from the base edge, and so on, gradually moving towards the vertex of the pyramid forming the laser beam reflection mirror 25. Practically, some lines of spots S1, S2 will be followed, involving a portion of the reflecting surface 25A near the base. Then, the laser beam is moved on the adjacent surface 25A to repeat the process, generating a series of spots on the reflecting surface and, thus, on the tissue of the vaginal canal. The process is repeated on all four faces. As it will be explained below, to avoid non-uniformity due to the edges of the pyramid and the bars 27, the whole process may be repeated rotating the retractor 19, and therefore the pyramidal laser beam reflection mirror 25, by a suitable angle, for instance 45°.

Figure 10B:
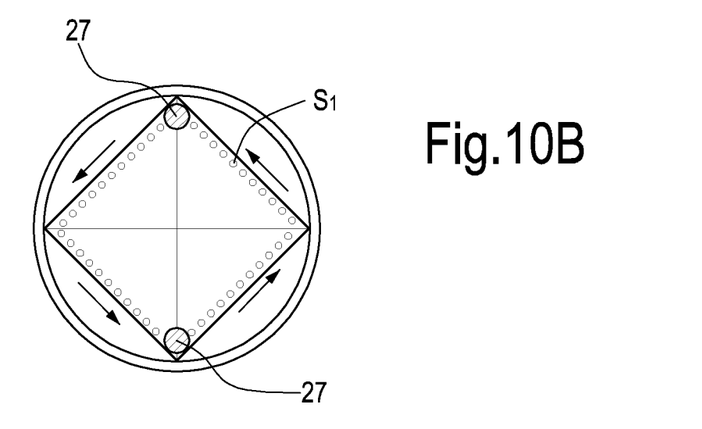
Figure 10C:
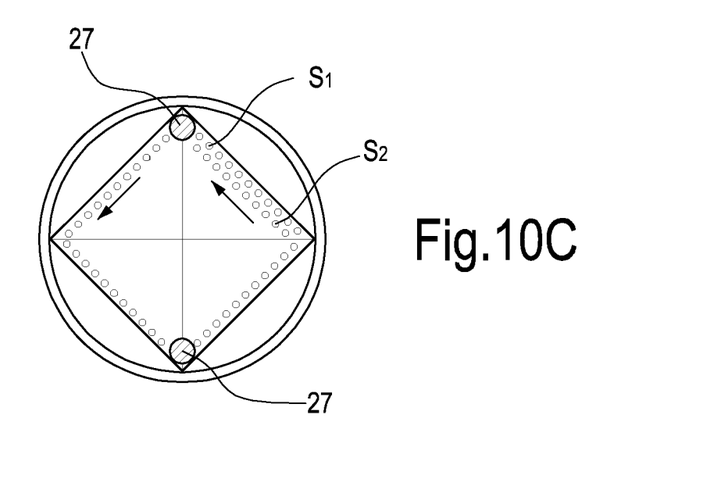

In other embodiments the laser beam may be moved in a substantially circular manner to be reflected in sequence by each of the four faces of the pyramidal laser beam reflection mirror 25 and moving gradually the laser beam so as to displace, at each revolution thereof around the axis of the pyramidal or truncated pyramidal laser beam reflection mirror, the reflection point of the beam from the base of the pyramid towards the vertex or vice versa, so as to invest an area of sufficient axial dimension of the tissue forming the vaginal canal. This operative mode is illustrated in FIGS. 10B and 10C. In FIG. 10B the first series of spots S1 is illustrated, created by moving the laser beam along the four base edges of the pyramidal laser beam reflection mirror. Once the closed path around the pyramid base has been completed, the beam is moved towards the vertex and along a closed path, forming the spots S2. In FIG. 10C the first phase is shown of this second movement of the beam with the formation of the spots on one of the four reflecting surfaces 25A of the laser beam reflection mirror 25. The process is repeated for a certain number of increasingly reducing closed paths while moving towards the vertex. Due to the effect of the laser beam reflection by means of the reflecting surfaces 25A, spots are therefore generated on the surface of the tissue of the vaginal canal, arranged according to substantially circular trajectories. In this case again, for each axial portion of the retractor 19 in the vaginal canal it is possible to perform the irradiation process twice, rotating the refractor 19 by an angle, for instance by 45°, between one process and the other, to avoid non-uniformity in the treatment.

In other embodiments the laser beam may be controlled to make a single revolution around the axis of the pyramidal laser beam reflection mirror, moving from one face to the other. In this case the distance between the reflecting surfaces of the pyramidal laser beam reflection mirror and the scanning mirrors 13A, 13B is constant. The trajectory of the laser beam can be increased or decreased to increase or decrease the area of the vaginal canal treated for each position of the retractor.

Advantageously, the four faces forming the reflecting surfaces 25A are inclined by about 45° with respect to the axis A-A of the retractor 19, so that the beam directed nearly parallel to the axis A-A (disregarding the slight inclination necessary to bring the beam in an intermediate area of each reflecting surface 25A) is reflected in a substantially orthogonal direction to the axis A-A and therefore nearly perpendicularly to the surface of the vaginal canal, inside which the retractor 19 has been inserted.

Controlling the scanning mirrors 13A, 13B as described above, it is therefore possible to treat a "slice" of the vaginal canal wall having a not-negligible dimension in the direction of the axis A-A of the retractor 19. Once this area of the vaginal canal has been treated, the retractor 19 can be moved by one step in axial direction, so as to treat in sequence the subsequent area or slice of vaginal canal.

In advantageous embodiments of the method described above, the laser beam is controlled so that for each position of the retractor 19 the laser beam is controlled to make a trajectory involving a limited portion of the pyramidal or truncated pyramidal laser beam reflection mirror, typically in the order of some millimeters, near the base. The axial extension of the mirror portion used is proportional to the "slice" of vaginal canal treated for each position of the retractor 19. The back or forward movement of the retractor 19 between one treatment phase and the subsequent one is preferably equal to the width of the treated "slice" so that, once the treatment is completed, all the inner surface of the vaginal canal has been subjected to the laser effect.

Figure 8:
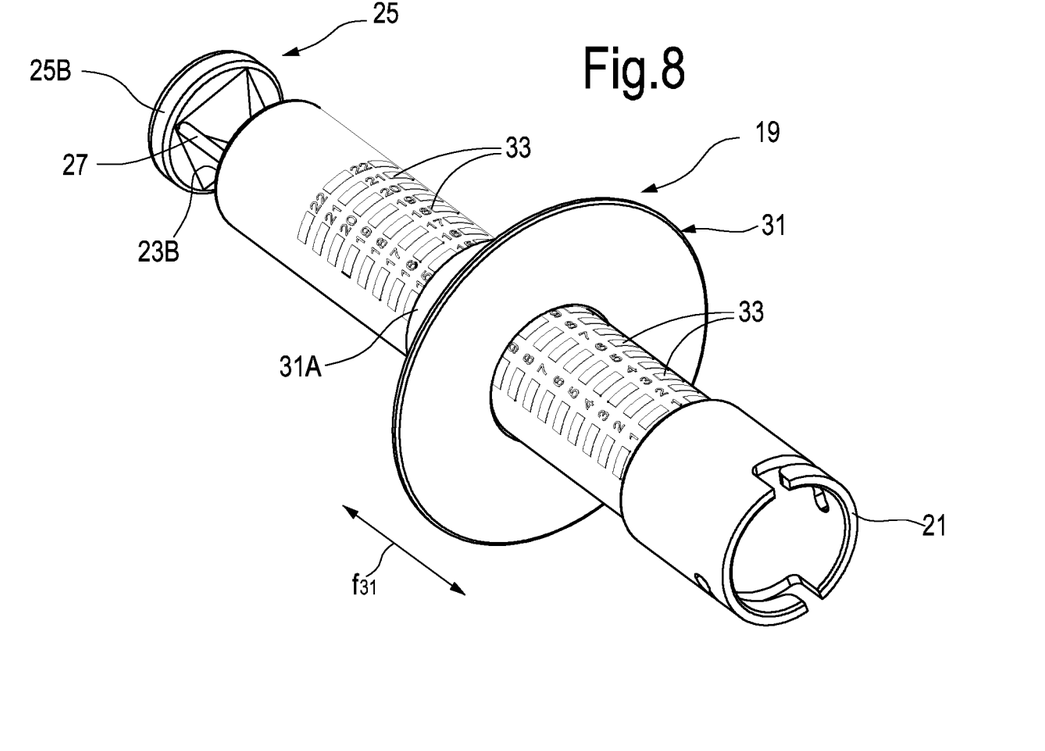
FIG. 8 is an axonometric view of the retractor.

The movement for gradually removing the retractor 19 from the vaginal canal may be better controlled using an element acting as a reference stop on the outside of the vaginal canal, as better shown in FIG. 8.

To this end, in some embodiments a disc-shaped element 31 is provided, mounted on the outside of the cylindrical body 23 of the retractor 19. The disc-shaped element 31, provided, if necessary, with an adequate collar 31A to increase the support surface on the cylindrical body 23 of the retractor 19, and the cylindrical body 23 of the retractor 19 slide with respect to each other according to the double arrow f31 (FIG. 8), so as to modify the distance between the laser beam reflection mirror 25 and the disc-shaped stop element 31 and consequently the depth of insertion of the retractor in the vaginal canal.

In some advantageous embodiments, reference marks 33 may be provided on the outer surface of the retractor 19, facilitating the operator in positioning and moving gradually the retractor 19 with respect to the disc-shaped stop element 31. The operator can rest the disc-shaped stop element on the vulva structures at the entrance of the vaginal canal and, maintaining it in this position, move the cylindrical body 23 of the retractor 19 parallel to the axial extension of the same retractor 19, gradually extracting it from or inserting it into the vaginal canal, moving it from the end where there is the bayonet coupling 21 towards the opposite end, as the treatment of the vaginal canal tissues proceeds as described above.

The marks 33 allow the operator to clearly identify the position of the retractor 19 with respect to the disc-shaped element 31 so as to treat subsequent "slices" or portions of the vaginal canal gradually and step by step.

Substantially, the treatment method is as follows: the refractor 19 is positioned, with respect to the disc-shaped stop element 31, in correspondence of the mark closest to the bayonet coupling 21, so that the refractor 19 can be completely inserted inside the vaginal canal until the disc-shaped stop element 31 abuts the patient's body in correspondence of the vaginal canal entrance. The operator actuates the laser and the scanning mirrors 13A, 13B so that, under the control of the programmed electronic control unit, the laser beam treats the whole surface of the vaginal canal that can be achieved moving the laser beam along the reflecting surfaces 25A of the laser beam reflection mirror 25 from the base towards the vertex of the same mirror or vice versa.

Once the treatment has been completed, the operator partially removes the retractor 19 extracting it by one step, so that the disc-shaped element 31 is aligned with the subsequent mark. The distance between two adjacent marks, in the order of some millimeters, corresponds to the dimension in axial direction of the vaginal canal area that can be treated in a single phase, before moving the retractor.

The operation is repeated for the different positions of the retractor 19 with respect to the disc-shaped stop element 31 up to the entrance of the vaginal canal.

In other embodiments the operator can act reversely, treating firstly the area closest to the vaginal canal entrance and gradually continuing towards the inside of the canal.

In some embodiments the treatment of each slice or area of the vaginal canal is performed twice, rotating the retractor 19 for instance by 45° around its own axis A-A between the first and the second treatment, thus avoiding discontinuities or irregularities in treating the tissue in correspondence of the edges of the pyramidal laser beam reflection mirror 25, and in particular in correspondence of the bars 27. Rotating the retractor 19 only once by an angle different than 90° (in the illustrated example), for instance by 45°, there are no areas of the vaginal canal tissue remaining untreated or treated incompletely. A single rotation for each treatment depth is sufficient. It is also possible to perform a first treatment for all the depth of the canal extracting the retractor 19 step by step and then to rotate the retractor 19 for instance by 45° and repeat the treatment for the areas not treated during the first phase, proceeding step by step whilst the retractor in inserted again or vice versa in case the treatment has been started inserting the retractor step by step in the first phase.

The laser beam is advantageously pulsed and its movement in the space is preferably controlled so as to treat adjacent but non overlapping tissue portions. In some embodiments the laser beam may be controlled to generate pulses with particular shape, for instance of the type described in WO2011096003, whose content is incorporated in the present disclosure.

Figure 9:
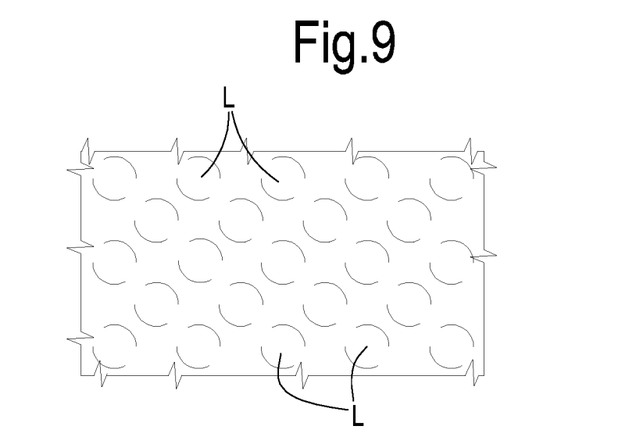
FIG. 9 is a scheme for fractional treatment of the vaginal tissue.

Practically, the laser beam directed towards the reflecting surfaces 25A of the pyramidal laser beam reflection mirror 25 can be controlled so as to involve volumes of vaginal canal tissue that are spaced from one another. FIG. 9 schematically shows an example of a sequence of spots formed by the laser beam and indicated with L, which can be provided directing the laser beam against the laser beam reflection mirror 25 and reflecting it by means of this mirror towards the wall of the vaginal canal. The laser beam involves for instance circular areas of tissue spaced from one another by means of areas not involved by the beam. Practically, the scanning mirrors 13A, 13B can control the movement of the laser beam so as to position it sequentially at each of the various points indicated in FIG. 9. In some embodiments the laser pulse may be synchronized with the movement of the scanning mirrors 13A, 13B, so that the laser pulse is generated only when the scanning mirrors are fixed in the position necessary to invest each single volume of the vaginal canal tissue. In some embodiments, the laser beam may be controlled so that in each position—defined by the scanning mirrors—more than one laser pulse is "shot" on the same tissue portion, for instance from two to four pulses.

FIG. 9 schematically shows three rows of spots L generated by controlling the laser beam as described above. Each row is generated arranging the scanning mirrors 13A, 13B so as to direct the laser beam on the respective side reflecting surface 25A of the pyramidal laser beam reflection mirror 25 at a substantially constant distance from the base edge. Subsequent rows are generated by moving the beam towards the vertex of the pyramid. Investing tissue volumes spaced from one another by means of the laser beam pulses in the spots L the tissue recovery time is much shorter than with a continuous treatment or a treatment wherein the spots of the laser beam overlap so as to treat the whole surface of the vaginal canal.

In the above description specific reference has been made to particularly advantageous embodiments for treating the vaginal canal. It should be however understood that a device of the type described above can be also used to treat tissues surrounding an orifice of different nature, for instance for treating the anal orifice, or an orifice provided surgically in a mass that is usually compact, i.e. usually devoid of orifices. The laser beam directed by means of the reflecting system and the scanning system described herein can be used for instance for surgical operations of ablation and/or cut inside a cavity, canal or orifice. The operations can be performed by means of an endoscopy visual system associated with the retractor, or arranged outside by means of ultra-sounds or other imaging technology.

In the description above a retractor 19 has been illustrated, provided with a pyramidal laser beam reflection mirror and with a deflection system for deflecting a laser beam to convey it towards the side wall of the vaginal canal or other natural or surgically obtained orifice, to treat the tissue surface. In a further embodiment, the retractor may be provided with means for acquiring images of the treated surface. In some embodiments the image acquisition system is integrated in the retractor and especially in the pyramidal laser beam reflection mirror.

Figure 12:
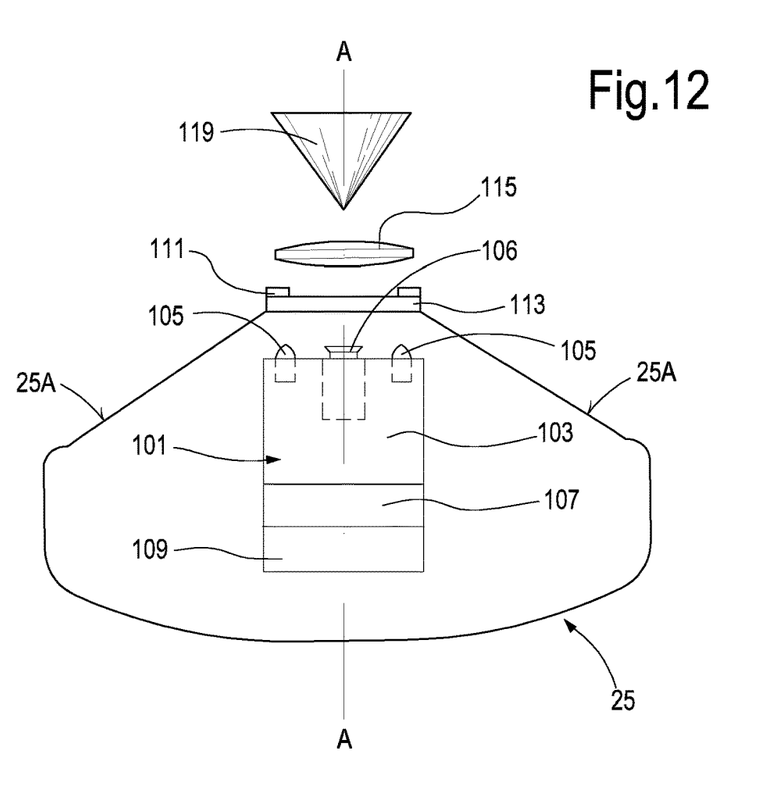
FIG. 12 is a schematic section of a pyramidal laser beam reflection mirror with an integrated image acquisition camera and an image acquisition mirror to be used with a retractor of the type described herein.

FIG. 12 illustrates a schematic section of a pyramidal laser beam reflection mirror, indicated again with reference number 25, which can be designed like the laser beam reflection mirror 25 described with reference to the previous embodiment. The laser beam reflection mirror 25 may be inserted in a retractor 19 of the type described above. In the embodiment of FIG. 12 a vision system, indicated as a whole with number 101, may be housed inside of the volume defined by the reflecting surfaces 25A of the laser beam reflection mirror 25. The system 101 may comprise a camera or a micro-camera 103 with a lens 106. The system 101 may also comprise lighting means 105. In some embodiments the lighting means 105 may comprise LEDs or other low-consumption emitters. The camera or micro-camera 103 and the lighting means 105 may be powered by means of a battery 107, preferably a rechargeable battery.

The system 101 may also comprise a radio transmitting electronic circuit 109 to transmit the images acquired by means of the camera or micro-camera 103. A suitable antenna, indicated for instance with 111, may be associated with the laser beam reflection mirror 25 and the radio transmitting circuit 109. In the illustrated embodiment, the antenna 111 is arranged on the lower base of the truncated pyramidal laser beam reflection mirror 25; it should be however understood that said antenna may be also arranged in a different position, for instance in correspondence of the upper base of the truncated pyramidal laser beam reflection mirror 25.

In advantageous embodiments the lower base of the pyramidal or truncated pyramidal laser beam reflection mirror 25 may be formed by or closed by a window 113, made of a material transparent to the wavelength at which the camera or micro-camera 103 shoots the images and to the radiation of the lighting means 105. A lens or optical system 115 may be associated with the window 113 to collect the images reflected by means of a reflecting system that collects the images of the wall of the vaginal canal, or other orifice, inside which the retractor 19 is inserted, and conveys these images towards the lens 106 of the camera or micro-camera 103. In some embodiments the reflecting system comprises a preferably conical or truncated conical image acquisition mirror 119 for acquiring the images coming from the side wall of the canal inside which the retractor 19 is inserted, and reflects the images, even if distorted, through the lens or other optical system 115 towards the lens 106 of the camera or micro-camera 103. In some embodiments the lens or optical system 115 may be omitted.

In some advantageous embodiments the image acquisition mirror 119 is coaxial or nearly coaxial with the pyramidal or truncated pyramidal laser beam reflection mirror 25, as schematically indicated in FIG. 12, where A-A indicates the common axis of the two mirrors.

Figure 13:
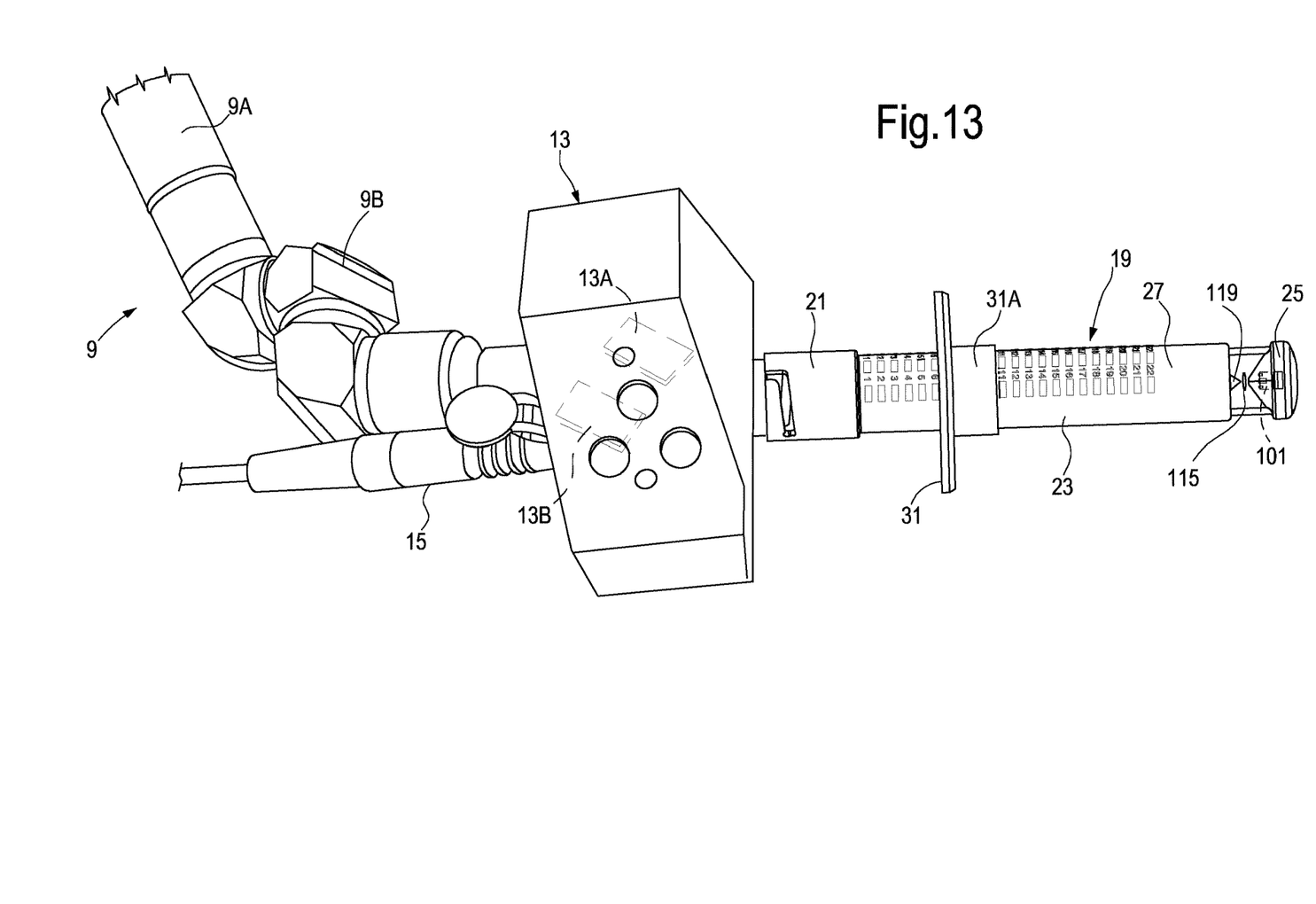
FIG. 13 is a side view of a retractor equipped with a laser beam reflection mirror and image acquisition mirror according to FIG. 12.

FIG. 13 is an overall view of the members described above and illustrated in FIG. 12, arranged in the retractor 19.

With this arrangement the camera or micro-camera 103 can acquire the images of the surface subjected to the laser treatment, preferably the side surface of the vaginal canal or of other treated orifice, immediately after the passage of the laser beam, thanks to the arrangement of the conical or truncated conical image acqustion mirror 119 with respect to the pyramidal or truncated pyramidal laser beam reflection mirror 25.

The electronics inside the pyramidal or truncated pyramidal laser beam reflection mirror 25 may be encapsulated in a sealed case to allow washing and sterilizing operations without damaging the inner mechanisms. The batteries 109 may be recharged for instance by means of an induction system without the need for electric contacts.

In the embodiments of FIGS. 12 and 13 to acquire images of the side wall this latter is lighted by means of lighting bodies or lighting means 105 housed inside the pyramidal or truncated pyramidal laser beam reflection mirror 25. In other embodiments the lighting system may be arranged outside the electronics contained inside the pyramidal or truncated pyramidal laser beam reflection mirror 25. Light emitting elements may be for instance provided, e.g. LEDs housed in the housing 13 together with the scanning mirrors 13A, 13B and preferably upstream thereof. The light beams generated by these sources can be deviated by means of the scanning mirrors 13A, 13B towards the reflecting surfaces 25A of the pyramidal or truncated pyramidal laser beam reflection mirror 25. The lighting beams are reflected laterally by means of the faces or surfaces of the pyramidal or truncated pyramidal laser beam reflection mirror 25. Thanks to the greater diameter of the lighting beams with respect to the laser beams, it is possible to use the same laser beam reflection mirror 25 to reflect both the laser beams and the lighting beams towards the side wall of the vaginal canal or other treated orifice, so as to light this surface and acquire, by means of the image acquisition mirror 119, the images that will be then transmitted towards a central processing unit, for instance through a radio transmission system or other wireless system 109.

Figure 11:
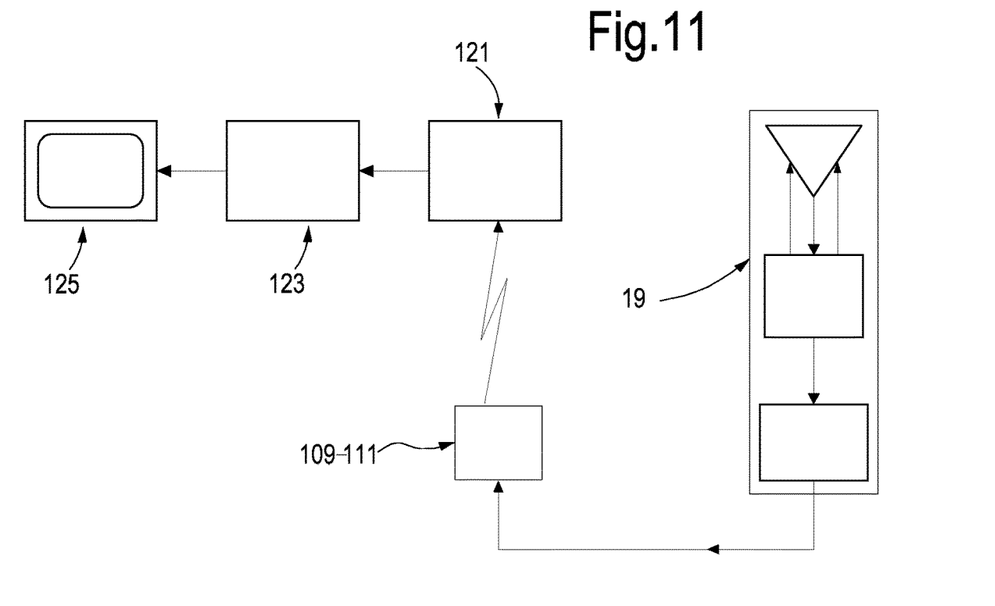
FIG. 11 is a functional block diagram of a system comprising a retractor with an image acquisition camera and an image processing unit.

FIG. 11 schematically shows a retractor 19 with a generic wireless system 119 for transmitting the images towards a receiving system schematically indicated with 121 and interfaced with a processing unit 123 showing the result of the image processing on a monitor 125 or on another suitable interface. The processing unit 123 may be provided with known software for correcting the optical distortion of the acquired images due to the conical shape of the reflecting surface of the image acquisition mirror 119.

Figures 14, 15:
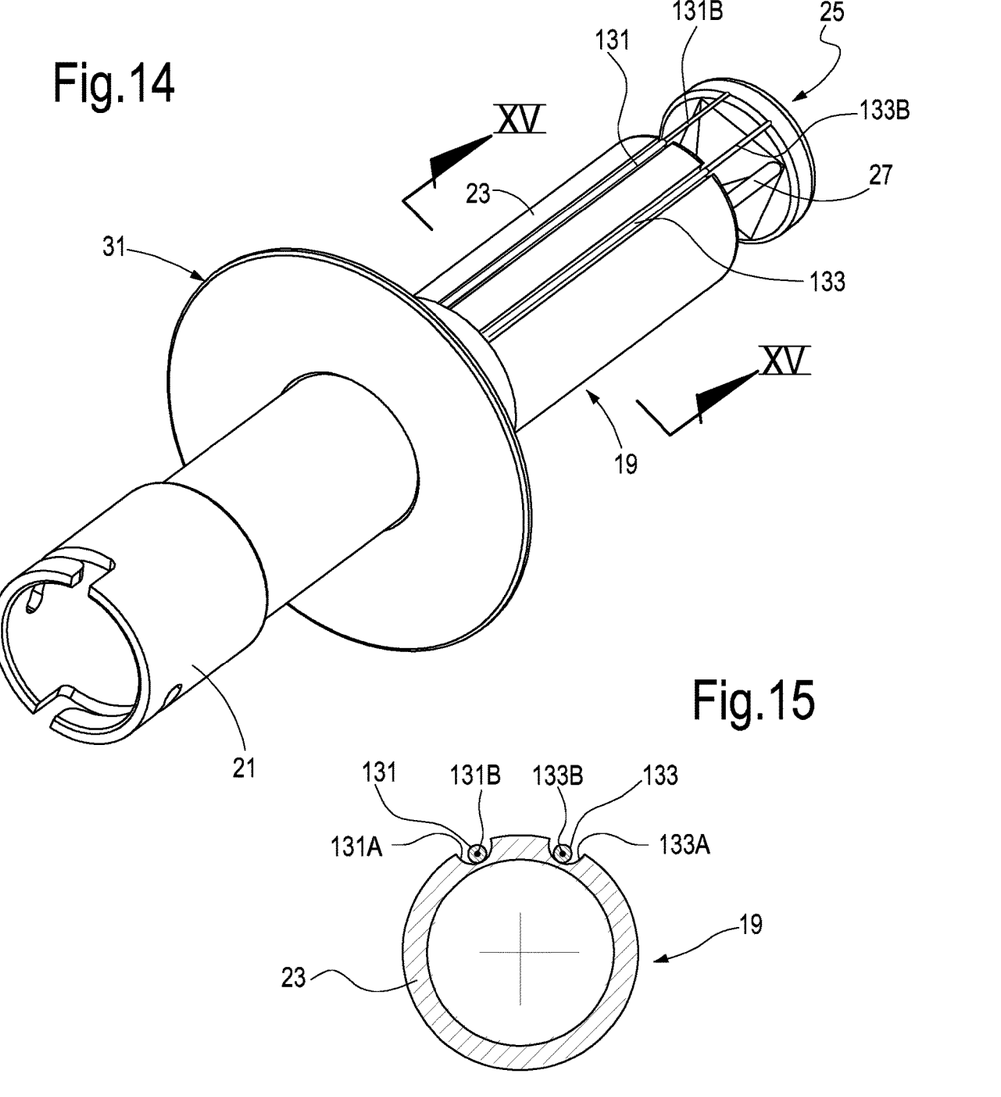
FIG. 14 is a side view of a retractor with an integrated electrode system for radio-frequency treatment.
FIG. 15 is a local section according to XV-XV of FIG. 14.

According to further embodiments, the device may be improved by including therein radio-frequency treatment functionality for radio-frequency treatment of the tissues forming the side wall of the vaginal canal and/or of other natural or surgically obtained orifices. FIGS. 14 and 15 show a possible configuration of electrodes for applying radio-frequency current. They may be used in combination with the image acquisition system or without it, i.e. they may be integrated in a device designed according to any one of the embodiments described above.

In some embodiments, as illustrated in FIGS. 14 and 15, two electrodes 131 and 133 may be applied on the outer wall of the cylindrical body 23. The electrodes 131 and 133 have preferably linear extension and extend for a part or the whole length of the cylindrical body 23. In some embodiments the electrodes 131 and 133 may be housed in grooves 131A and 133A (see FIG. 15) provided on the outer surface of the cylindrical body 23.

Advantageously, the electrodes 131 and 133 are parallel to each other and to the longitudinal axis of the cylindrical body 23 of the retractor 19.

In some embodiments, the two electrodes 131 and 133 are close to each other, i.e. they are arranged at the end of a limited arc, for instance a 45° arc, preferably 35° arc, and more preferably 30° or less of the substantially circular extension of the wall with circular section forming the cylindrical body 23. In vaginal applications, the distance between the electrodes 131 and 133 is such that it is possible to irradiate the areas adjacent to the clitoris and the urethra with RF currents. These RF currents have therapeutic effects in the treatment of incontinence in women. In practical embodiments of the treatment method, the retractor may be moved so that the irradiation with radio-frequency currents involves the whole vaginal canal, not only in correspondence of the clitoris but also in depth, in the areas adjacent to the bladder.

The two electrodes 131 and 133 can be connected, by means of suitable connectors (not shown), to a radio-frequency current source housed in the main apparatus. The apparatus, constituted by or housed inside the central unit 14, may be programmed so as to coordinate the radio-frequency treatment and the laser treatment of the tissues. These two treatments can be consecutive, simultaneous or partially simultaneous, i.e. only partially overlapped. In some embodiments it is possible for instance to apply the radio-frequency current immediately before applying the laser and, if necessary, during laser application.

To localize the radio-frequency treatment in the area where the laser beam is applied, in advantageous embodiments the electrodes 131, 133 are insulated for a part of their longitudinal extension and are uncovered for instance in the area 131B, 133B in correspondence of the free space where the laser beam reflected by means of the laser beam reflection mirror 25 passes. The portion of the electrodes 131, 133 housed in the seats or grooves 131A, 133A can be insulated. In this way the radio-frequency current is applied on tissues facing towards the pyramidal laser beam reflection mirror 25, which can be therefore treated simultaneously with the laser radiation and the radio-frequency current.

It is understood that the drawing only shows an example provided by way of a practical arrangement of the invention, which can vary in forms and arrangement without however departing from the scope of the concept underlying the invention. Any reference numerals in the appended claims are provided to facilitate reading of the claims with reference to the description and to the drawing, and do not limit the scope of protection represented by the claims.

The invention claimed is:

1. A device for treating at least one of a vaginal canal, a natural orifice and a surgically obtained orifice by means of a laser beam, the device comprising:
 a retractor for a wall of said canal or orifice associated with a laser beam scanning system, wherein:
 said retractor comprises one of a pyramidal laser beam reflection mirror and a truncated pyramidal laser beam reflection mirror, which is provided with a plurality of planar reflecting surfaces arranged around a retractor axis and inclined with respect thereto, and is located near a retractor distal end;
 the laser beam scanning system is configured and controlled to direct the laser beam sequentially towards each planar reflecting surface of the laser beam reflection mirror, a series of laser spots according to an irradiation treatment pattern being generated on each reflecting surface and being reflected thereby outside the retractor;
 said retractor has a substantially cylindrical hollow body, at a distal end whereof said laser beam reflection mirror is fixed;
 said retractor is configured to be inserted into at least one of the vaginal canal, the natural orifice and the surgically obtained orifice such that the laser beam is configured to be applied to a tissue of a user to treat the tissue;
 said laser beam reflection mirror is connected to said substantially cylindrical hollow body of the retractor by means of at least one spacer leaving a free space between the laser beam reflection mirror and the substantially cylindrical body of the retractor; and
 said at least one spacer is arranged at a corner of the laser beam reflection mirror.

2. A device according to claim 1, wherein said retractor comprises an image acquisition system for acquiring images of walls of the vaginal canal or other orifices, associated with said retractor.

3. A device according to claim 2, wherein an image acquisition mirror is associated with said laser beam reflection mirror.

4. A device according to claim 3, wherein the laser beam reflection mirror and the image acquisition mirror are substantially coaxial.

5. A device according to claim 4, wherein said laser beam reflection mirror and said image acquisition mirror are directed with respect to each other so that a lighting beam reflected by the laser beam reflection mirror illuminates a portion of the canal or orifice of which the image acquisition mirror reflects the image towards an image acquisition lens.

6. A device according to claim 1, wherein said laser beam reflection mirror has quadrangular and preferably square base.

7. A device according to claim 3, wherein the image acquisition mirror and the laser beam reflection mirror are substantially coaxial, with vertexes or smaller bases facing each other.

8. A device according to claim 2, wherein said image acquisition system comprises a camera housed in the laser beam reflection mirror.

9. A device according to claim 1, wherein said retractor has a substantially cylindrical hollow body, at a distal end whereof said laser beam reflection mirror is fixed.

10. A device according to claim 9, wherein an aperture is defined between the distal end of the substantially cylindrical hollow body and the laser beam reflection mirror, and through said aperture a free path extends for the laser beam reflected by the laser beam reflection mirror towards the wall of the canal or orifice in which the device is inserted.

11. A device according to claim 9, wherein at a proximal end of the substantially cylindrical hollow body an element is provided for coupling the retractor to a support containing the laser scanning system.

12. A device according to claim 9, wherein said laser beam reflection mirror is connected to a substantially cylindrical body of the retractor by means of one or more spacers leaving a free space between the laser beam reflection mirror and the substantially cylindrical body of the retractor.

13. A device according to claim 12, wherein said spacers are arranged at corners of the laser beam reflection mirror.

14. A device according to claim 1, further comprising:
 a stop cooperating with the retractor to control a depth to which the retractor is inserted into the canal or orifice and said stop and said retractor are preferably movable with respect to each other along an axial extension of the retractor.

15. A device according to claim 14, wherein said retractor has indicia for positioning the stop.

16. A device according to claim 1, wherein at least one electrode is arranged along the retractor and can be associated with a radio-frequency current source.

17. A device according to claim 1, wherein said retractor comprises an image acquisition system for acquiring images of walls of the vaginal canal or other orifices, associated with said retractor.

18. A device according to claim 9, wherein two electrodes are arranged along the retractor and can be associated with a radio-frequency current source, wherein said two electrodes extend along the substantially cylindrical hollow body of the retractor and emerge on an outer surface of the substantially cylindrical hollow body.

19. A device according to claim 18, wherein the two electrodes are parallel to one another.

20. A laser apparatus comprising a laser source, a waveguide and a device connected with said laser source through said waveguide, said device comprising a retractor for a wall of a canal or orifice associated with a laser beam scanning system, wherein said retractor comprises a pyramidal or truncated pyramidal laser beam reflection mirror, which is provided with a plurality of planar reflecting surfaces arranged around a retractor axis and inclined with respect thereto, and is located near a retractor distal end, the laser beam scanning system being configured and controlled to direct the laser beam sequentially towards each planar reflecting surface of the laser beam reflection mirror, a series of laser spots according to an irradiation treatment pattern being generated on each reflecting surface and being reflected thereby outside the retractor, wherein said retractor has a substantially cylindrical hollow body, at a distal end whereof said laser beam reflection mirror is fixed, said retractor being configured to be inserted into at least one of the vaginal canal, the natural orifice and the surgically obtained orifice such that the laser beam is configured to be applied to a tissue of a user to treat the tissue, said laser beam reflection mirror being connected to said substantially cylindrical hollow body of the retractor by means of at least one spacer leaving a free space between the laser beam reflection mirror and the substantially cylindrical body of the retractor, said at least one spacer being arranged at a corner of the laser beam reflection mirror.

21. A laser apparatus according to claim 20, wherein said laser source is a pulsed laser source, said retractor being configured to be inserted in the canal or orifice such that tissue associated with the canal or orifice is therapeutically treated via the laser beam.

22. A laser apparatus according to claim 20, wherein said laser source is a continuous laser source.

23. A laser apparatus according to claim 21, wherein the pulses have a duration between about 0.1 and about 10 ms.

24. A laser apparatus according to claim 20, wherein a wavelength of said laser source is between about 1000 nm and about 12,000 nm.

25. A laser apparatus according to claim 20, wherein said laser source has a power between about 2 and about 100 W.

26. A laser apparatus according to claim 20, wherein said source and said device are controlled so as to generate a pulsed treatment pattern, wherein a space between subsequent scanning points is between 0 and about 5,000 micrometers.

27. A laser apparatus according to claim 20, wherein a pulsed or continuous laser beam is controlled to remain on the same points repeating an emission duration up to 5 times a duration of a single emission.

28. A laser apparatus according to claim 20, further comprising an image receiving system for receiving images from said device.

29. A laser apparatus according to claim 28, wherein said image receiving system is a wireless system.

30. A laser apparatus according to claim 20, further comprising an image processing system to reduce or eliminate distortion of images collected by means of a curve mirror, in particular a conical or truncated conical mirror.

31. A laser apparatus according to claim 21, wherein the pulses have a duration between about 0.2 and about 2 ms.

32. A laser apparatus according to claim 20, wherein a wavelength of said laser source is 10,600 nm.

33. A laser apparatus according to claim 32, wherein said laser source is a $CO_2$ laser source.

34. A laser apparatus according to claim 20, wherein said laser source has a power between 10 and about 50 W.

35. A laser apparatus according to claim 20, wherein said laser source has a power between about 30 and about 50 W.

36. A laser apparatus according to claim 20, wherein said source and said device are controlled so as to generate a pulsed treatment pattern, wherein a space between subsequent scanning points is between about 50 and about 5,000 micrometers.

37. A laser apparatus according to claim 20, wherein said source and said device are controlled so as to generate a pulsed treatment pattern, wherein a space between subsequent scanning points is between about 200 and about 2,000 micrometers.

38. A laser apparatus for treating mucosa of a vaginal canal, comprising:
   a pulsed laser source having a wavelength between about 1000 nm and about 12,000 nm;
   a device configured to treat the vaginal canal, comprising a retractor for a wall of the vaginal canal and a laser beam scanning system associated with said retractor;
   a waveguide for conveying a laser beam towards said device, wherein said retractor comprises a pyramidal or truncated pyramidal laser beam reflection mirror, which is provided with a plurality of planar reflecting surfaces arranged around a retractor axis and inclined with respect thereto, and is located near a retractor distal end, wherein the laser beam scanning system is configured and controlled to direct the laser beam sequentially towards each planar reflecting surface of the laser beam reflection mirror, a series of laser spots according to an irradiation pattern being generated on each reflecting surface and being reflected thereby outside the retractor, said retractor comprising an image acquisition system for acquiring images of walls of the vaginal canal or other orifices, associated with said retractor, wherein an image acquisition mirror is associated with said laser beam reflection mirror, the laser beam reflection mirror and the image acquisition mirror being substantially coaxial, said laser beam reflection mirror and said image acquisition mirror being directed with respect to each other so that a lighting beam reflected by the laser beam reflection mirror illuminates a portion of the canal or orifice of which the image acquisition mirror reflects the image towards an image acquisition lens.

39. A device for treating at least one of a vaginal canal, a natural orifice and a surgically obtained orifice by means of a laser beam, the device comprising:
   a retractor for a wall of said canal or orifice associated with a laser beam scanning system, wherein:
      said retractor comprises one of a pyramidal laser beam reflection mirror and a truncated pyramidal laser beam reflection mirror, which is provided with a plurality of planar reflecting surfaces arranged around a retractor axis and inclined with respect thereto, and is located near a retractor distal end;

the laser beam scanning system is configured and controlled to direct the laser beam sequentially towards each planar reflecting surface of the laser beam reflection mirror, a series of laser spots according to an irradiation treatment pattern being generated on each reflecting surface and being reflected thereby outside the retractor;

said retractor comprises an image acquisition system for acquiring images of walls of the vaginal canal or other orifices, associated with said retractor;

an image acquisition mirror is associated with said laser beam reflection mirror;

the laser beam reflection mirror and the image acquisition mirror are substantially coaxial; and said laser beam reflection mirror and said image acquisition mirror are directed with respect to each other so that a lighting beam reflected by the laser beam reflection mirror illuminates a portion of the canal or orifice of which the image acquisition mirror reflects the image towards an image acquisition lens.

40. A device according to claim 39, wherein said image acquisition mirror has a conical or truncated-conical reflecting surface.

41. A device according to claim 39, further comprising a wireless system for transmitting images from the device to an image processing apparatus.

42. A device for treating at least one of a vaginal canal, a natural orifice and a surgically obtained orifice by means of a laser beam, the device comprising:

a retractor for a wall of said canal or orifice associated with a laser beam scanning system, wherein:

said retractor comprises one of a pyramidal laser beam reflection mirror and a truncated pyramidal laser beam reflection mirror, which is provided with a plurality of planar reflecting surfaces arranged around a retractor axis and inclined with respect thereto, and is located near a retractor distal end;

the laser beam scanning system is configured and controlled to direct the laser beam sequentially towards each planar reflecting surface of the laser beam reflection mirror, a series of laser spots according to an irradiation treatment pattern being generated on each reflecting surface and being reflected thereby outside the retractor; and at least one electrode is arranged along the retractor and can be associated with a radio-frequency current source.

43. A device according to claim 42, wherein at least one electrode is arranged along the retractor and can be associated with a radio-frequency current source, wherein said electrode extends along the substantially cylindrical hollow body of the retractor and emerge on an outer surface of the substantially cylindrical hollow body.

* * * * *